United States Patent [19]

Tonelli et al.

[11] Patent Number: 4,896,529
[45] Date of Patent: Jan. 30, 1990

[54] PERFLUORO-2,3,4-TRIMETHYLPENTHANE AND PROCESS FOR THE PREPARATION THEREOF

[75] Inventors: Claudio Tonelli; Vito Tortelli, both of Milan, Italy

[73] Assignee: Ausimont S.p.A., Milan, Italy

[21] Appl. No.: 178,011

[22] Filed: Apr. 5, 1988

[30] Foreign Application Priority Data

Apr. 10, 1987 [IT] Italy .................................. 20060 A/87

[51] Int. Cl.⁴ ............................................. G01M 3/20
[52] U.S. Cl. ..................................................... 73/40.7
[58] Field of Search ................................ 73/40.7, 49.3

[56] References Cited

U.S. PATENT DOCUMENTS 4,154,092  5/1979  White et al. ........................ 73/49.3

Primary Examiner—Michael J. Tokar
Assistant Examiner—Joseph W. Roskos
Attorney, Agent, or Firm—Stevens, Davis, Miller & Mosher

[57] ABSTRACT

This invention relates to perfluoro-2,3,4-trimethylpentane of formula (I):

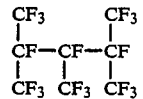

and to its use as an indicator fluid in the method NID for carrying out the Gross leak test.

1 Claim, No Drawings

PERFLUORO-2,3,4-TRIMETHYLPENTHANE AND PROCESS FOR THE PREPARATION THEREOF

The perfluoroalkanes, thanks to their characteristics of non-toxicity, uniflammability, chemical and thermal resistance and unusual electric properties, find growing possibilities of use in many technologically advanced industrial sectors.

There are known several processes for preparing same. For examples, perfluoroalkanes are obtained by fluorination with $COF_3$ of mainly aromatic hydrocarbons. E. J. Barber, J. Burodon, I. W. Parson, J. C. Tatlow Tetrahedron vol. 28, pages 43–52 (1972).

Otherwise, perfluoroalkanes are prepared by direct fluorination of aliphatic hydrocarbons with elemental fluorine (R. J. Lagow, J. L. Margreve Progr. Inorg. Chem. vol 26, pages 161–210 (1979).

Both these processes are not selective because they give rise, besides to the desired perfluoroalkanes, also to by-product mixtures containing partially hydrogenated fluoroalkanes or to perfluoroalkanes having a lower number of carbon atoms, and that in an uncontrolled way. In fact, fluorination leads to an easy rupture of simple C-C bonds.

Of course, that limits the industrial utilization of these processes.

Also the electrochemical technique for fluorinating hydrogenated substrates is little utilizable to fluorinate hydrocarbons: in fact, it is essentially utilized to fluorinate carboxylic and sulphonic acids.

U.S. Pat. No. 3,962,358 describes a process for fluorinating perfluoroolefins with elemental fluorine in order to obtain the corresponding perfluoroalkanes with good yields.

This process, however, permits to obtain perfluoroalkanes with 6 and 9 carbon atoms and having, respectively, boiling points of 60° and 130° C.; it is not possible to synthetize perflouroalkanes with intermediate boiling points.

For a few appliances in the field of electronics it is necessary, conversely, to have available fluids having boiling points ranging from 120° to 130° C. as they can be advantageously used as cooling fluids to cool laser circuits. and electronic circuits in general, or as fluids for tests in electronics, such as for example the Gross Leak Test by method NID in accordance with MIL STD 883C (Aug. 25, 1983) conforming to procedure F.

Available on the market are fluorohydrocarbon fluids for electronics having boiling points up to 102° C., such as for example FC® 75 and 77 produced by 3M, or fluorohydrocarbon fluids having boiling point.

For a few appliances in the field of electronics it is necessary, conversely, to have available fluids having boiling points ranging from 100° to 130° C., as they can be advantageously used as cooling fluids to cool laser circuits and electronic circuits in general, or as fluids for tests in electronics, such as for example the Gross Leak Test by method NID in accordance with MIL STD 883C (Aug. 25, 1983) conforming to procedure F.

Available on the market are fluorohydrocarbon fluids for electronics having boiling points up to 102° C., such as for example FC® 75 and 77 produced by 3M, or fluorohydrocarbon fluids having boiling points higher than 170° C.(FC® 43, boiling point=175° C., and FC®70, boiling point=215° C.), however there are not available fluids with intermediate boiling points, nor it is advisable to use mixture of above-cited products in order to obtain fluids with boiling points in the above-mentioned range. Thus, it is an object of the present invention to provide a new perfluoroalkane by a more selective process as compared with the ones of the art.

Another object of the present invention is to obtain a thermally stable perfluoroalkane, which can be utilized in the electronic industry both as a cooling fluid and as fluid for testing electronic circuits.

The above objects have been achieved by obtaining a new fluorinated compound, i.e. perfluoro-2,3,4-trimethylpentane of formula:

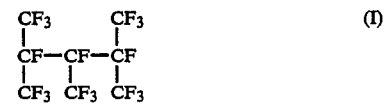

prepared by subjecting to fluorination with elemental fluorine, in the presence of U.V. radiations at temperatures comprised between −40° and +40° C., the hexafluoropropene trimer,

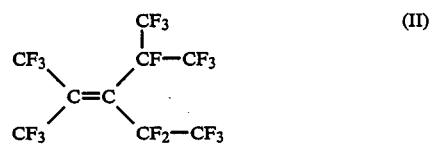

eventually in the presence of the olefin of formula (III)

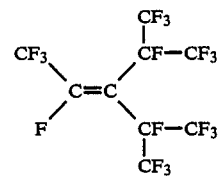

The trimers of formula (II) and (III) were obtained according to the process as described in U.S. Pat. No. 3,917,724.

The reaction is preferably conducted at temperatures ranging from 10° to 35° C., U.V. irradiation is obtained by means of a high pressure mercury discharge lamp.

Generally, fluorination is conducted in the presence or in the absence of an inert gas as a diluent.

The reaction can be conveniently carried out in the presence of a perfluorinated inert solvent preferably a perfluoropolyether having a molecular weight comprised in the range of from 800 to 2000

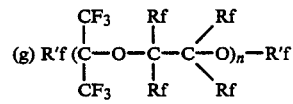

and selected from one of the following classes:

(a) $CF_3O\,(C_2F_4O)_p(CF_2O)_q\text{-}CF_3$ wherein p and q are integers and the p/q ratio ranges from 1 to 0.5. The units $C_2F_4O$ and $CF_2O$ are randomly distributed along the chain;

(b) $RfO(C_3F_6O)_m(CFXO)_nRf$ wherein $Rf=CF_3$, $C_2F_5$, $C_3F_7$ X is either F or $CF_3$ m and n are integers such as to fulfil the conditions that the molecular weight be higher than 800 and lower than 2000;

(c) $C_3F_7O(C_3F_6O)_xC_2F_5$ wherein x is an integer such as to fulfil the condition that the molecular weight be higher than 800 and lower than 2000;

(d) $R'f(CF_2CF_2O)_nR'f$ wherein n is an integer such as to fulfil the above mentioned condition and $R'f=CF_3$ or $C_2F_5$;

(e) $A(CF_2CF_2CF_2O)_n B$ wherein n is an integer such as to fulfil the above conditions $A=F$ or $R'f$, $B=R'f$ or $C_3F_7$;

(f) perfluropolyethers containing repeating units $C_2F_4O$, $(C_3F_6)$ $(CFXO)$ and having a molecular weight comprised between 800 and 2000;

wherein R'f is a perfluoroalkyl group n is at least 8, Rf is F or a perfluoroalkyl group.

The perfluoropentane of the present invention is obtained in the presence of new highly branched perfluoroalkanes, object of another Italian Patent Application No. 20061 A/87, filed concurrently with the present Application.

The products according to the present invention can be easily separated by the other reaction products with good yields by rectification with high purity degree.

Furthermore, as it has a boiling point of 115° C., it is highly suited to be used for cooling laser circuits such as those of aeronautic systems and for the cited tests in electronics.

The following example is given for merely illustrative purposes and is not to be construed as a limitation of the present invention.

EXAMPLE 1

Into a quartz reactor having an optical path of 5 mm and a volume of 2,000 ml, 300 g (0.76 moles) of product (II) as defined hereinabve were charged and after generation of a $N_2$ atmosphere in the reactor, a flow of $F_2$ and $N_2$ (1:1) equal to 2 l/h was introduced. While maintaining the inner temperature at 33° C., irradiation was simultaneously carried out using a high pressure mercury discharge lamp type Hanau TQ 150 (wave length ranging from 254 to 400 nanometers).

The reaction trend was followed by gas-chromatographic analysis. After 24 hours, the starting olefin was no longer present. $F_2$ flow and U.V. irradiation were stopped and 310 g of a colorless fluid having a boiling point of 115° C. at 760 mm of Hg and the following structure (NMR[19] F δ, $CFCl_3$):

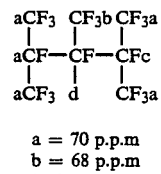

a = 70 p.p.m
b = 68 p.p.m
c,d 169–170 p.p.m

A fraction essentially consisting of perfluoroalkanes having 9 carbon atoms remained in the vessel.

EXAMPLE 2

150 g of a mixture containing 94% by weight of the perfluoroolefin of formula II and 6% by weight of the perfluorolefin of formula III and 150 g of a perfluoropolyether having a molecular weight 1800 and belonging to class (b) were loaded in the reactor according to example 1 while maintaining the inner temperature at 15° C., irradiation was simultaneously carried out using the U.V. lamp of Example 1.

At the end of the reaction 135 g of perfluorinated products were removed from the solvent by means of distillation and subsequently by rectification, 56 g of product of formula (I) are recuperated (yield 41%).

What is claimed is:

1. Process for carrying out the Gross leak test according to *MIL-STD* 883C *Rules, Condition F*, in which perfluoro-2,3,4-trimethylpentane is used as an indicator fluid.

* * * * *